(12) United States Patent
Rieping

(10) Patent No.: US 7,332,309 B2
(45) Date of Patent: Feb. 19, 2008

(54) PROCESS FOR THE PREPARATION OF L-AMINO ACIDS USING STRAINS OF THE ENTEROBACTERIACEAE FAMILY WHICH CONTAIN AN ENHANCED SUCC OR SUCD GENE

(75) Inventor: Mechthild Rieping, Bielefeld (DE)

(73) Assignee: Degussa AG, Duesseldorf (DE)

( * ) Notice: Subject to any disclaimer, the term of this patent is extended or adjusted under 35 U.S.C. 154(b) by 558 days.

(21) Appl. No.: 10/484,162

(22) PCT Filed: Jul. 3, 2002

(86) PCT No.: PCT/EP02/07375

§ 371 (c)(1),
(2), (4) Date: Jan. 20, 2004

(87) PCT Pub. No.: WO03/008615

PCT Pub. Date: Jan. 30, 2003

(65) Prior Publication Data

US 2006/0003423 A1    Jan. 5, 2006

Related U.S. Application Data

(60) Provisional application No. 60/306,869, filed on Jul. 23, 2001.

(30) Foreign Application Priority Data

Jul. 8, 2001 (DE) ................................ 101 35 053

(51) Int. Cl.
*C12P 13/08* (2006.01)
*C12P 13/06* (2006.01)
*C12N 9/00* (2006.01)
*C12N 1/21* (2006.01)
*C07H 21/04* (2006.01)

(52) U.S. Cl. ................ 435/115; 435/116; 435/183; 435/252.3; 435/252.33; 536/23.2

(58) Field of Classification Search .................. None
See application file for complete search history.

(56) References Cited

U.S. PATENT DOCUMENTS 4,278,765 A    7/1981  Debabov et al. ............ 438/172

FOREIGN PATENT DOCUMENTS

| EP | 0 237 819 | 9/1987 |
|---|---|---|
| EP | 0 643 135 | 3/1995 |
| EP | 0 994 190 | 4/2000 |
| EP | 1 103 611 | 5/2001 |
| JP | 03 236786 | 10/1991 |
| WO | 99 53035 | 10/1999 |
| WO | 03 008600 | 1/2003 |
| WO | 03 008605 | 1/2003 |
| WO | 03 008606 | 1/2003 |
| WO | 03 008607 | 1/2003 |
| WO | 03 008608 | 1/2003 |
| WO | 03 008609 | 1/2003 |
| WO | 03 008610 | 1/2003 |
| WO | 03 008611 | 1/2003 |
| WO | 03 008612 | 1/2003 |
| WO | 03 008613 | 1/2003 |
| WO | 03 008614 | 1/2003 |

OTHER PUBLICATIONS

Walshaw D L et al.: "Regulation of the TCA cycle and the general amino acid permease by overflow metabolism in Rhizobium leguminosarum", MICROBIOLOGY, vol. 143, No. 7, pp. 2209-2221 1997.
Schuster S et al. : "Detection of elementary flux modes in biochemical networks: a promising tool for pathway analysis and metabolic engineering" Trends in Biotechnology. vol. 17, No. 2. pp. 53-60 Feb. 1999.
Michal G: "Biochemical pathways: an atlas of biochemistry and molecular biology". John Wiley & Sons Inc. and Spektrum Akademischer Verlag, 1999.
Buck D et al. : "Primary structure of the succinyl-CoA synthetase of *Escherichia coli* ". BIOCHEMISTRY, vol. 24, pp. 6245-6252 1985.
Buck D et al.: "Overexpression and site-directed mutagenesis of hte succinyl-CoA synthetase of *Escherichia coli* and nucleotide sequence of a gene (g30) that is adjacent to the suc operon". The Biochemical Journal . vol. 260, No. 3, pp. 737-747, Jun. 15, 1989.
Birney M et al. : Novel mechanisms of *Escherichia coli* succinyl-coenzyme A synthetase regulation, Journal of Bacteriology, vol. 178, No. 10, pp. 2883-2889 May 1996.
Kraemer R:"Genetic and physiological approaches for the production of amino acids." Journal of Biotechnology, vol. 45, No. 1, pp. 1-21, 1996.
Jetten M S M et al. : "Recent advances in the physiology and genetics of amino acid-producing bacteria." CRC Critical Reviews in Biotechnology, vol. 15, No. 1, pp. 73-103 1995.
U.S. Appl. No. 10/076,416, filed Feb. 19, 2002, Rieping, et al.
U.S. Appl. No. 10/114,073, filed Apr. 3, 2002, Rieping, et al.
U.S. Appl. No. 10/114,043, filed Apr. 3, 2002, Rieping et al.
U.S. Appl. No. 10/114,048, filed Apr. 3, 2002, Rieping, et al.
U.S. Appl. No. 10/616,309, filed Jul. 10, 2003, Rieping, et al.
U.S. Appl. No. 10/483,417, filed Jan. 20, 2004, Rieping.
U.S. Appl. No. 10/484,198, filed Jan. 20, 2004, Rieping.
U.S. Appl. No. 10/483,416, filed Jan. 20, 2004, Rieping.
U.S. Appl. No. 10/484,162, filed Jan. 20, 2004, Rieping.
U.S. Appl. No. 10/491,893, filed Apr. 15, 2004, Rieping, et al.

*Primary Examiner*—Elizabeth Slobodyansky
(74) *Attorney, Agent, or Firm*—Oblon, Spivak, McClelland, Maier & Neustadt, P.C.

(57) ABSTRACT

The invention relates to a process for the preparation of L-amino acids, in particular L-threonine, in which the following steps are carried out: a) fermentation of microorganisms of the Enterobacteriaceae family which produce the desired L-amino acid and in which at least one or more of the genes chosen from the group consisting of sucC and sucD, or nucleotide sequences which code for these, is or are enhanced, in particular over-expressed, b) concentration of the desired L-amino acid in the medium or in the cells of the bacteria, and c) isolation of the desired L-amino acid.

11 Claims, 1 Drawing Sheet

SEQUENCE LISTING

<160> NUMBER OF SEQ ID NOS: 2

<210> SEQ ID NO 1
<211> LENGTH: 33
<212> TYPE: DNA

-continued

```
<213> ORGANISM: Artificial Sequence
<220> FEATURE:
<223> OTHER INFORMATION: synthetic oligonucleotide

<400> SEQUENCE: 1
ggatctagac gattactgaa ggatggacag aac                          33

<210> SEQ ID NO 2
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 2
gagaagcttg gcgagggcta tttcttatta c                            31
```

PROCESS FOR THE PREPARATION OF L-AMINO ACIDS USING STRAINS OF THE ENTEROBACTERIACEAE FAMILY WHICH CONTAIN AN ENHANCED SUCC OR SUCD GENE

FIELD OF THE INVENTION

This invention relates to a process for the preparation of L-amino acids, in particular L-threonine, using strains of the Enterobacteriaceae family in which at least one or more of the genes chosen from the group consisting of sucC and sucD is (are) enhanced.

PRIOR ART

L-Amino acids, in particular L-threonine, are used in human medicine and in the pharmaceuticals industry, in the foodstuffs industry and very particularly in animal nutrition.

It is known to prepare L-amino acids by fermentation of strains of Enterobacteriaceae, in particular Escherichia coli (E. coli) and Serratia marcescens. Because of their great importance, work is constantly being undertaken to improve the preparation processes. Improvements to the process can relate to fermentation measures, such as e.g. stirring and supply of oxygen, or the composition of the nutrient media, such as e.g. the sugar concentration during the fermentation, or the working up to the product form, by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the threonine analogue α-amino-β-hydroxyvaleric acid (AHV), or are auxotrophic for metabolites of regulatory importance and produce L-amino acid, such as e.g. L-threonine, are obtained in this manner.

Methods of the recombinant DNA technique have also been employed for some years for improving the strain of strains of the Enterobacteriaceae family which produce L-amino acids, by amplifying individual amino acid biosynthesis genes and investigating the effect on the production.

OBJECT OF THE INVENTION

The object of the invention is to provide new measures for improved fermentative preparation of L-amino acids, in particular L-threonine.

SUMMARY OF THE INVENTION

The invention provides a process for the fermentative preparation of L-amino acids, in particular L-threonine, using microorganisms of the Enterobacteriaceae family which in particular already produce L-amino acids and in which at least one or more of the nucleotide sequence(s) which code(s) for the sucC and sucD genes is (are) enhanced.

DETAILED DESCRIPTION OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Threonine is particularly preferred.

The term "enhancement" in this connection describes the increase in the intracellular activity of one or more enzymes or proteins in a microorganism which are coded by the corresponding DNA, for example by increasing the number of copies of the gene or genes, using a potent promoter or a gene or allele which codes for a corresponding enzyme or protein with a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

The process comprises carrying out the following steps:
a) fermentation of microorganisms of the Enterobacteriaceae family in which one or more of the genes chosen from the group consisting of sucC and sucD, or nucleotide sequences which code for these, is (are) enhanced, in particular over-expressed,
b) concentration of the corresponding L-amino acid in the medium or in the cells of the microorganisms of the Enterobacteriaceae family, and
c) isolation of the desired L-amino acid, constituents of the fermentation broth and/or the biomass in its entirety or portions (>0 to 100%) thereof optionally remaining in the product.

The microorganisms which the present invention provides can produce L-amino acids from glucose, sucrose, lactose, fructose, maltose, molasses, optionally starch, optionally cellulose or from glycerol and ethanol. They are representatives of the Enterobacteriaceae family chosen from the genera Escherichia, Erwinia, Providencia and Serratia. The genera Escherichia and Serratia are preferred. Of the genus Escherichia the species Escherichia coli and of the genus Serratia the species Serratia marcescens are to be mentioned in particular.

Suitable strains, which produce L-threonine in particular, of the genus Escherichia, in particular of the species Escherichia coli, are, for example
Escherichia coli TF427
Escherichia coli H4578
Escherichia coli KY10935
Escherichia coli VNIIgenetika MG442
Escherichia coli VNIIgenetika M1
Escherichia coli VNIIgenetika 472T23
Escherichia coli BKIIM B-3996
Escherichia coli kat 13
Escherichia coli KCCM-10132.

Suitable L-threonine-producing strains of the genus Serratia, in particular of the species Serratia marcescens, are, for example
Serratia marcescens HNr21
Serratia marcescens TLr156
Serratia marcescens T2000.

Strains from the Enterobacteriaceae family which produce L-threonine preferably have, inter alia, one or more genetic or phenotypic features chosen from the group consisting of: resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidin, resistance to rifampicin, resistance to valine analogues, such as, for example, valine hydroxamate, resistance to purine analogues, such as, for example, 6-dimethylaminopurine, a need for L-methionine, optionally a partial and compensable need for L-isoleucine, a need for meso-diaminopimelic acid, auxotrophy in respect of threonine-containing dipeptides, resistance to L-threonine, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, optionally an ability for sucrose utilization, enhancement of the threonine operon, enhancement of homoserine dehydrogenase I-aspartate kinase I, preferably of the feed back resistant form, enhancement of homoserine kinase, enhancement of threonine synthase, enhancement of aspartate kinase, optionally of the feed back resistant form, enhancement of aspartate semialdehyde dehydrogenase, enhancement of phosphoenol pyruvate carboxylase, optionally of the feed back resistant form, enhancement of phosphoenol pyruvate synthase, enhancement of transhydrogenase, enhancement of the RhtB gene product, enhancement of the RhtC gene product, enhancement of the YfiK gene product, enhancement of a pyruvate carboxylase, and attenuation of acetic acid formation.

It has been found that microorganisms of the *Enterobacteriaceae* family produce L-amino acids, in particular L-threonine, in an improved manner after enhancement, in particular over-expression, of at least one or more of the genes chosen from the group consisting of sucC and sucD.

The nucleotide sequences of the genes of *Escherichia coli* belong to the prior art and can also be found in the genome sequence of *Escherichia coli* published by Blattner et al. (Science 277: 1453-1462 (1997)).

The following information, inter alia, on the sucC and sucD genes is known from the prior art:

sucC gene:
Description: β-Sub-unit of succinyl-CoA synthetase
EC No. 6.2.1.5
Reference: Buck et al.; Biochemistry 24(22): 6245-6252 (1985); Buck and Guest; Biochemical Journal 260(3): 737-747 (1989); Cronan and Laporte; In: Neidhardt (ed), *Escherichia coli* and *Salmonella*, American Society for Microbiology, Washington, D.C., USA: 206-216 (1996)
Accession No.: AE000176 sucD gene:
Description: α-Sub-unit of succinyl-CoA synthetase
EC No. 6.2.1.5
Reference: Buck et al.; Biochemistry 24(22): 6245-6252 (1985); Buck and Guest; Biochemical Journal 260(3): 737-747 (1989); Cronan and Laporte; In: Neidhardt (ed), *Escherichia coli* and *Salmonella*, American Society for Microbiology, Washington, D.C., USA: 206-216 (1996)
Accession No.: AE000176

The nucleic acid sequences can be found in the databanks of the National Center for Biotechnology Information (NCBI) of the National Library of Medicine (Bethesda, Md., USA), the nucleotide sequence databank of the European Molecular Biologies Laboratories (EMBL, Heidelberg, Germany or Cambridge, UK) or the DNA databank of Japan (DDBJ, Mishima, Japan).

The genes described in the text references mentioned can be used according to the invention. Alleles of the genes which result from the degeneracy of the genetic code or due to "sense mutations" of neutral function can furthermore be used.

To achieve an enhancement, for example, expression of the genes or the catalytic properties of the proteins can be increased. The two measures can optionally be combined.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-threonine production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Chang and Cohen (Journal of Bacteriology 134: 1141-1156 (1978)), in Hartley and Gregori (Gene 13: 347-353 (1981)), in Amann and Brosius (Gene 40: 183-190 (1985)), in de Broer et al. (Proceedings of the National Academy of Sciences of the United States of America 80: 21-25 (1983)), in LaVallie et al. (BIO/TECHNOLOGY 11: 187-193 (1993)), in PCT/US97/13359, in Llosa et al. (Plasmid 26: 222-224 (1991)), in Quandt and Klipp (Gene 80: 161-169 (1989)), in Hamilton et al. (Journal of Bacteriology 171: 4617-4622 (1989)), in Jensen and Hammer (Biotechnology and Bioengineering 58: 191-195 (1998)) and in known textbooks of genetics and molecular biology.

Plasmid vectors which are capable of replication in *Enterobacteriaceae*, such as e.g. cloning vectors derived from pACYC184 (Bartolomé et al.; Gene 102: 75-78 (1991)), pTrc99A (Amann et al.; (Gene 69: 301-315 (1988)) or pSC101 derivatives (Vocke and Bastia; Proceedings of the National Academy of Sciences of the United States of America 80 (21): 6557-6561 (1983)) can be used. A strain transformed with a plasmid vector, where the plasmid vector carries at least one or more of the genes chosen from the group consisting of sucC and sucD, or nucleotide sequences which code for these, can be employed in a process according to the invention.

It is also possible to transfer mutations which affect the expression of the particular gene into various strains by sequence exchange (Hamilton et al.; Journal of Bacteriology 171: 4617-4622 (1989)), conjugation or transduction.

It may furthermore be advantageous for the production of L-amino acids, in particular L-threonine, with strains of the *Enterobacteriaceae* family, in addition to enhancement of one or more of the genes chosen from the group consisting of sucC and sucD, for one or more enzymes of the known threonine biosynthesis pathway or enzymes of anaplerotic metabolism or enzymes for the production of reduced nicotinamide adenine dinucleotide phosphate or enzymes of glycolysis or PTS enzymes or enzymes of sulfur metabolism to be enhanced.

Thus, for example, at the same time one or more of the genes chosen from the group consisting of the thrABC operon which codes for aspartate kinase, homoserine dehydrogenase, homoserine kinase and threonine synthase (U.S. Pat. No. 4,278,765), the pyc gene of *Corynebacterium glutamicum* which codes for pyruvate carboxylase (WO 99/18228), the pps gene which codes for phosphoenol pyruvate synthase (Molecular and General Genetics 231(2): 332-336 (1992)), the ppc gene which codes for phosphoenol pyruvate carboxylase (Gene 31: 279-283 (1984)), the pntA and pntB genes which code for transhydrogenase (European Journal of Biochemistry 158: 647-653 (1986)), the rhtB gene which imparts homoserine resistance (EP-A-0 994 190), the mqo gene which codes for malate:quinone oxidoreductase (WO 02/06459), the rhtc gene which imparts threonine resistance (EP-A-1 013 765), the thrE gene of *Corynebacterium glutamicum* which codes for the threonine export protein (WO 01/92545), the gdhA gene which codes for glutamate dehydrogenase (Nucleic Acids Research 11: 5257-5266 (1983); Gene 23: 199-209 (1983)), the hns gene which codes for the DNA-binding protein HLP-II (Molecular and General Genetics 212: 199-202 (1988)), the pgm gene which codes for phosphoglucomutase (Journal of Bacteriology 176: 5847-5851 (1994)), the fba gene which codes for fructose biphosphate aldolase (Biochemical Journal 257: 529-534 (1989)), the ptsH gene of the ptsHIcrr operon which codes for the phosphohistidine protein hexose phosphotransferase of the phosphotransferase system PTS (Journal of Biological Chemistry 262: 16241-16253 (1987)), the ptsI gene of the ptsHIcrr operon which codes for enzyme I of the phosphotransferase system PTS (Journal of Biological Chemistry 262: 16241-16253 (1987)), the crr gene of the ptsHIcrr operon which codes for the glucose-specific IIA component of the phosphotransferase system PTS (Journal of Biological Chemistry 262: 16241-16253 (1987)), the ptsG gene which codes for the glucose-specific IIBC component (Journal of Biological Chemistry 261: 16398-16403 (1986)), the lrp gene which codes for the regulator of the leucine regulon (Journal of Biological Chemistry 266: 10768-10774 (1991)), the mopB gene which codes for 10 Kd chaperone (Journal of Biological Chemistry 261: 12414-12419 (1986)) and is also known by the name groES, the ahpC gene of the ahpCF operon which codes for the small sub-unit of alkyl hydroperoxide reductase (Proceedings of the National Academy of Sciences of the United States of America 92: 7617-7621 (1995)), the ahpF gene of the ahpCF operon which codes for the large sub-unit of alkyl hydroperoxide reductase (Proceedings of the National Academy of Sciences of the United States of America 92: 7617-7621 (1995)), the cysK gene which codes for cysteine synthase A (Journal of Bacteriology 170: 3150-3157 (1988)), the cysB gene which codes for the regulator of the cys regulon (Journal of Biological Chemistry 262: 5999-6005 (1987)), the cysJ gene of the cysJIH operon which codes for the flavoprotein of NADPH sulfite reductase (Journal of Biological Chemistry 264: 15796-15808 (1989), Journal of Biological Chemistry 264: 15726-15737 (1989)), the cysI gene of the cysJIH operon which codes for the haemoprotein of NADPH sulfite reductase (Journal of Biological Chemistry 264: 15796-15808 (1989), Journal of Biological Chemistry 264: 15726-15737 (1989)), the cysH gene of the cysJIH operon which codes for adenylyl sulfate reductase (Journal of Biological Chemistry 264: 15796-15808 (1989), Journal of Biological Chemistry 264: 15726-15737 (1989)), the phoE gene which codes for protein E of the outer cell membrane (Journal of Molecular Biology 163 (4): 513-532 (1983)), the malE gene which codes for the periplasmic binding protein of maltose transport (Journal of Biological Chemistry 259 (16): 10606-10613 (1984)), the pykF gene which codes for fructose-stimulated pyruvate kinase I (Journal of Bacteriology 177 (19): 5719-5722 (1995)), the pfkB gene which codes for 6-phosphofructokinase II (Gene 28 (3): 337-342 (1984)), the talB gene which codes for transaldolase B (Journal of Bacteriology 177 (20): 5930-5936 (1995)), the rseA gene of the rseABC operon which codes for a membrane protein with anti-sigmae activity (Molecular Microbiology 24 (2): 355-371 (1997)), the rseC gene of the rseABC operon which codes for a global regulator of the sigmaE factor (Molecular Microbiology 24 (2): 355-371 (1997)), the soda gene which codes for superoxide dismutase (Journal of Bacteriology 155 (3): 1078-1087 (1983)), the phoB gene of the phoBR operon which codes for the positive regulator PhoB of the pho regulon (Journal of Molecular Biology 190 (1): 37-44 (1986)), the phoR gene of the phoBR operon which codes for the sensor protein of the pho regulon (Journal of Molecular Biology 192 (3): 549-556 (1986)), the sucA gene of the sucABCD operon which codes for the decarboxylase sub-unit of 2-ketoglutarate dehydrogenase (European Journal of Biochemistry 141 (2): 351-359 (1984)) and the sucB gene of the sucABCD operon which codes for the dihydrolipoyltranssuccinase E2 sub-unit of 2-ketoglutarate dehydrogenase (European Journal of Biochemistry 141 (2): 361-374 (1984))

can be enhanced, in particular over-expressed.

It may furthermore be advantageous for the production of L-amino acids, in particular L-threonine, in addition to enhancement of one or more of the genes chosen from the group consisting of sucC and sucD, for one or more of the genes chosen from the group consisting of the tdh gene which codes for threonine dehydrogenase (Journal of Bacteriology 169: 4716-4721 (1987)), the mdh gene which codes for malate dehydrogenase (E.C. 1.1.1.37) (Archives in Microbiology 149: 36-42 (1987)), the gene product of the open reading frame (orf) yjfA (Accession Number AAC77180 of the National Center for Biotechnology Information (NCBI, Bethesda, Md., USA)), the gene product of the open reading frame (orf) ytfP (Accession Number AAC77179 of the National Center for Biotechnology Information (NCBI, Bethesda, Md., USA)), the pckA gene which codes for the enzyme phosphoenol pyruvate carboxykinase (Journal of Bacteriology 172: 7151-7156 (1990)), the poxB gene which codes for pyruvate oxidase (Nucleic Acids Research 14(13): 5449-5460 (1986)), the aceA gene which codes for the enzyme isocitrate lyase (Journal of Bacteriology 170: 4528-4536 (1988)), the dgsA gene which codes for the DgsA regulator of the phosphotransferase system (Bioscience, Biotechnology and Biochemistry 59: 256-251 (1995)) and is also known under the name of the mlc gene, the fruR gene which codes for the fructose repressor (Molecular and General Genetics 226: 332-336 (1991)) and is also known under the name of the cra gene and the rpoS gene which codes for the sigma$^{38}$ factor (WO 01/05939) and is also known under the name of the katF gene, to be attenuated, in particular eliminated or for the expression thereof to be reduced.

The term "attenuation" in this connection describes the reduction or elimination of the intracellular activity of one or more enzymes (proteins) in a microorganism which are coded by the corresponding DNA, for example by using a weak promoter or a gene or allele which codes for a corresponding enzyme with a low activity or inactivates the corresponding enzyme (protein) or gene, and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

It may furthermore be advantageous for the production of L-amino acids, in particular L-threonine, in addition to enhancement of one or more of the genes chosen from the group consisting of sucC and sucD, to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention can be cultured in the batch process (batch culture), the fed batch process (feed process) or the repeated fed batch process (repetitive feed process). A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and optionally cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the abovementioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 25° C. to 45° C., and preferably 30° C. to 40° C. Culturing is continued until a maximum of L-amino acids or L-threonine has formed. This target is usually reached within 10 hours to 160 hours.

The analysis of L-amino acids can be carried out by anion exchange chromatography with subsequent ninhydrin derivation, as described by Spackman et al. (Analytical Chemistry 30: 1190-1206 (1958)), or it can take place by reversed phase HPLC as described by Lindroth et al. (Analytical Chemistry 51: 1167-1174 (1979)).

The process according to the invention is used for the fermentative preparation of L-amino acids, such as, for example, L-threonine, L-isoleucine, L-valine, L-methionine, L-homoserine and L-lysine, in particular L-threonine.

The present invention is explained in more detail in the following with the aid of embodiment examples.

The minimal (M9) and complete media (LB) for *Escherichia coli* used are described by J. H. Miller (A Short Course in Bacterial Genetics (1992), Cold Spring Harbor Laboratory Press). The isolation of plasmid DNA from *Escherichia coli* and all techniques of restriction, ligation, Klenow and alkaline phosphatase treatment are carried out by the method of Sambrook et al. (Molecular Cloning—A Laboratory Manual (1989) Cold Spring Harbor Laboratory Press). Unless described otherwise, the transformation of *Escherichia coli* is carried out by the method of Chung et al. (Proceedings of the National Academy of Sciences of the United States of America 86: 2172-2175 (1989)).

The incubation temperature for the preparation of strains and transformants is 37° C.

EXAMPLE 1

Construction of the Expression Plasmid pTrc99AsucCD

The sucC and sucD genes from *E. coli* K12 are amplified using the polymerase chain reaction (PCR) and synthetic oligonucleotides. Starting from the nucleotide sequence of the sucC and sucD genes in *E. coli* K12 MG1655 (Accession Number AE000176, Blattner et al. (Science 277: 1453-1462 (1997)), PCR primers are synthesized (MWG Biotech, Ebersberg, Germany). The sequences of the primers are modified such that recognition sites for restriction enzymes are formed. The recognition sequence for XbaI is chosen for the sucCD1 primer and the recognition sequence for HindIII for the sucCD2 primer, which are marked by underlining in the nucleotide sequence shown below:

```
sucCD1:
                                       (SEQ ID No. 1)
5' - GGATCTAGACGATTACTGAAGGATGGACAGAAC - 3' sucCD2:
                                       (SEQ ID No. 2)
5' - GAGAAGCTTGGCGAGGGCTATTTCTTATTAC - 3'
```

The chromosomal *E. coli* K12 MG1655 DNA employed for the PCR is isolated according to the manufacturer's instructions with "Qiagen Genomic-tips 100/G" (QIAGEN, Hilden, Germany). A DNA fragment approx. 2100 bp in size can be amplified with the specific primers under standard PCR conditions (Innis et al. (1990) PCR Protocols. A Guide to Methods and Applications, Academic Press) with Pfu-DNA polymerase (Promega Corporation, Madison, USA).

The PCR product is cleaved with the restriction enzymes XbaI and HindIII and ligated with the vector pTrc99A (Pharmacia Biotech, Uppsala, Sweden), which has been digested with the enzymes XbaI and HindIII. The *E. coli* strain XL1-Blue MRF (Stratagene, La Jolla, USA) is transformed with the ligation batch and plasmid-carrying cells are selected on LB agar, to which 50 μg/ml ampicillin are added. Successful cloning can be demonstrated after plasmid DNA isolation by control cleavage with the enzymes EcoRV, HpaI and SspI. The plasmid is called pTrc99AsucCD (FIG. 1).

EXAMPLE 2

Preparation of L-Threonine with the Strain MG442/pTrc99AsucCD

The L-threonine-producing *E. coli* strain MG442 is described in the patent specification U.S. Pat. No. 4,278,765 and deposited as CMIM B-1628 at the Russian National Collection for Industrial Microorganisms (VKPM, Moscow, Russia).

The strain MG442 is transformed with the expression plasmid pTrc99AsucCD described in example 1 and with the vector pTrc99A and plasmid-carrying cells are selected on LB agar with 50 μg/ml ampicillin. The strains MG442/pTrc99AsucCD and MG442/pTrc99A are formed in this manner. Selected individual colonies are then multiplied further on minimal medium with the following composition: 3.5 g/l Na$_2$HPO$_4$.2H$_2$O, 1.5 g/l KH$_2$PO$_4$, 1 g/l NH$_4$Cl, 0.1 g/l MgSO$_4$.7H$_2$O, 2 g/l glucose, 20 g/l agar, 50 mg/l ampicillin. The formation of L-threonine is checked in batch cultures of 10 ml contained in 100 ml conical flasks. For this, 10 ml of preculture medium of the following composition: 2 g/l yeast extract, 10 g/l (NH$_4$)$_2$SO$_4$, 1 g/l KH$_2$PO$_4$, 0.5 μl MgSO$_4$.7H$_2$O, 15 g/l CaCO$_3$, 20 g/l glucose, 50 mg/l ampicillin are inoculated and the batch is incubated for 16 hours at 37° C. and 180 rpm on an ESR incubator from Kuhner AG (Birsfelden, Switzerland).

250 μl portions of this preculture are transinoculated into 10 ml of production medium (25 g/l (NH$_4$)$_2$SO$_4$, 2 g/l KH$_2$PO$_4$, 1 g/l MgSO$_4$.7H$_2$O, 0.03 g/l FeSO$_4$.7H$_2$O, 0.018 g/l MnSO$_4$*7H$_2$O, 30 g/l CaCO$_3$, 20 g/l glucose, 50 mg/l ampicillin) and the batch is incubated for 48 hours at 37° C. The formation of L-threonine by the starting strain MG442 is investigated in the same manner, but no addition of ampicillin to the medium takes place. After the incubation the optical density (OD) of the culture suspension is determined with an LP2W photometer from Dr. Lange (Düsseldorf, Germany) at a measurement wavelength of 660 nm.

The concentration of L-threonine formed is then determined in the sterile-filtered culture supernatant with an amino acid analyzer from Eppendorf-BioTronik (Hamburg, Germany) by ion exchange chromatography and post-column reaction with ninhydrin detection.

The result of the experiment is shown in Table 1.

TABLE 1

| Strain | OD (660 nm) | L-Threonine g/l |
|---|---|---|
| MG442 | 5.6 | 1.4 |
| MG442/pTrc99A | 3.8 | 1.3 |
| MG442/pTrc99AsucCD | 5.7 | 2.6 |

Figure 1:
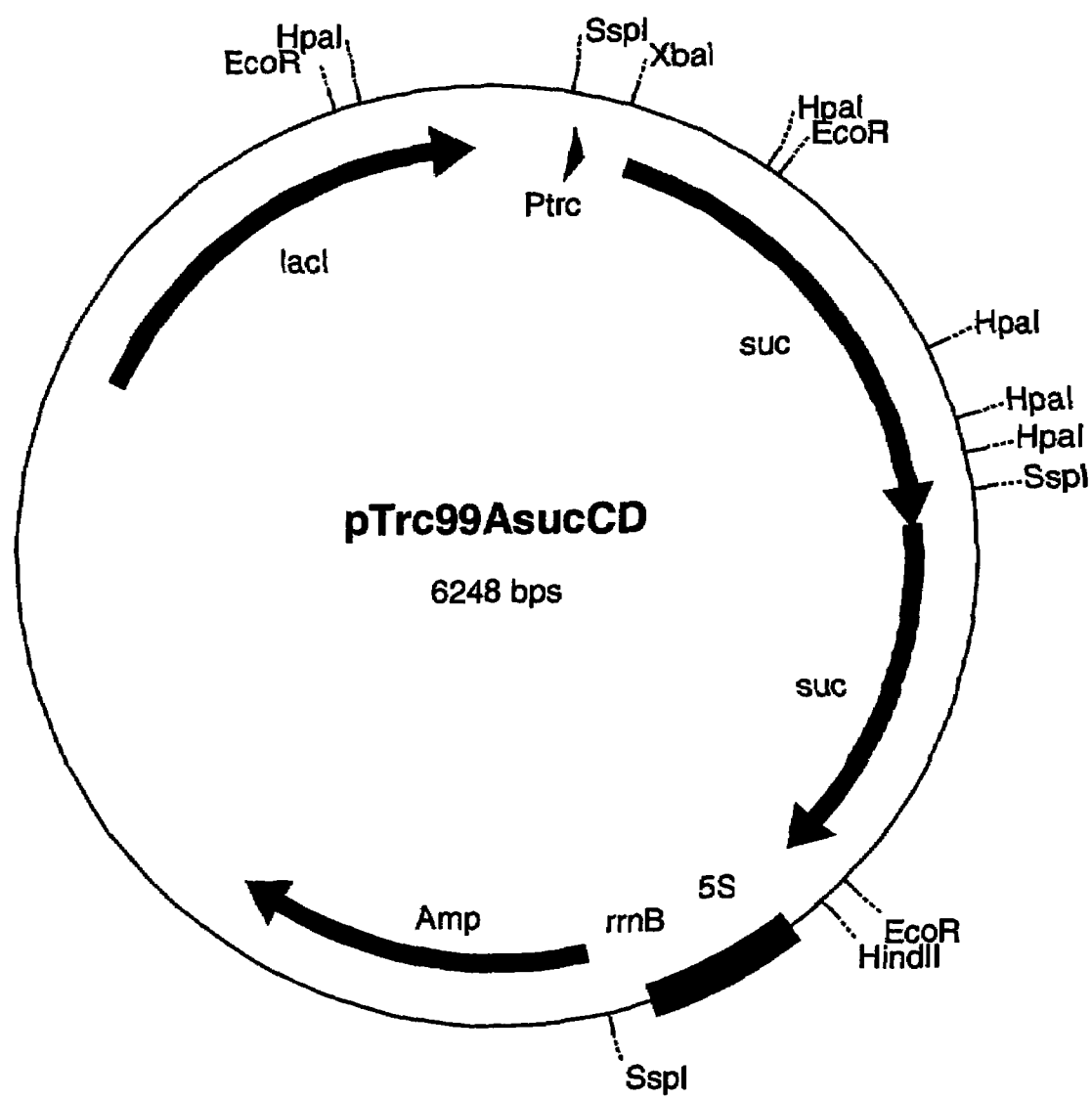
FIG. 1: Map of the plasmid pTrc99AsucCD containing the sucC and sucD genes.

The length data are to be understood as approx. data. The abbreviations and designations used have the following meaning:

Amp: Ampicillin resistance gene
lacI: Gene for the repressor protein of the trc promoter
Ptrc: trc promoter region, IPTG-inducible
sucC: Coding region of the sucC gene
sucD: Coding region of the sucD gene
5S: 5S rRNA region
rrnBT: rRNA terminator region The abbreviations for the restriction enzymes have the following meaning EcoRV: Restriction endonuclease from *Escherichia coli* B946
HindIII: Restriction endonuclease from *Haemophilus influenzae*
HpaI: Restriction endonuclease from *Haemophilus parainfluenzae*
SspI: Restriction endonuclease from *Sphaerotilus* species ATCC 13925
XbaI: Restriction endonuclease from *Xanthomonas campestris*

What is claimed is:

1. A process for the preparation of a L-amino acid selected from the group consisting of L-threonine, L-valine, L-isoleucine and L-lysine, comprising:
   a) fermenting in a medium a microorganism of the Enterobacteriaceae family which produces the L-amino acid and in which the *E. coli* sucC and/or sucD gene is/are overexpressed by increasing the copy number or by being placed under a strong promoter;
   b) concentrating the L-amino acid in the medium or in the cells of the microorganism, and
   c) isolating the L-amino acid.

2. The process of claim 1, wherein the microorganism of the Enterobacteriaceae family is of the genus *Escherichia*.

3. The process of claim 1, wherein the microorganism of the Enterobacteriaceae family is an *Escherichia coli*.

4. The process of claim 1, wherein constituents of the fermentation broth and/or the biomass in its entirety or portions thereof are isolated as a solid product together with the L-amino acid.

5. The process of claim 1, wherein the number of copies of the sucC and/or sucD gene is increased.

6. The process of claim 1, wherein the sucC and/or sucD gene is/are placed under a strong promoter.

7. The process of claim 1, wherein, in the microorganism, the genes selected from the group consisting of:
   the *E.coli* thrABC operon which codes for aspartate kinase, homoserine dehydrogenase, homoserine kinase and threonine synthase, and
   the corynebacterium glutamicum pyc gene which codes for pyruvate carboxylase,
is/are overexpressed by increasing the copy number or by being placed under a strong promoter.

8. The process of claim 1, wherein the L-amino acid is L-threonine.

9. The process of claim 1, wherein the L-amino acid is L-lysine.

10. The process of claim 1, wherein the L-amino acid is L-valine.

11. The process of claim 1, wherein the L-amino acid is L-isoleucine.

* * * * *